(12) United States Patent
Zaman et al.

(10) Patent No.: US 10,710,056 B2
(45) Date of Patent: Jul. 14, 2020

(54) CERIA SUPPORTED PALLADIUM/CALCIUM CATALYST FOR HYDROGENATING CO₂ TO DIMETHYL ETHER

(71) Applicant: King Abdulaziz University, Jeddah (SA)

(72) Inventors: Sharif Fakhruz Zaman, Jeddah (SA); Ali Shan Malik, Jeddah (SA); Abdulrahim Ahmed Alzahrani, Jeddah (SA); Muhammad A. Daous, Jeddah (SA); Lachezar A. Petrov, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 16/176,565

(22) Filed: Oct. 31, 2018

(65) Prior Publication Data

US 2020/0129960 A1 Apr. 30, 2020

(51) Int. Cl.
*B01J 23/58* (2006.01)
*B01J 23/10* (2006.01)
(Continued)

(52) U.S. Cl.
CPC .............. *B01J 23/58* (2013.01); *B01J 23/10* (2013.01); *B01J 35/026* (2013.01);
(Continued)

(58) Field of Classification Search
CPC ............ C01B 3/326; C01B 2203/1041; C01B 2203/1064; B01J 23/58; B01J 35/026;
(Continued)

(56) References Cited

U.S. PATENT DOCUMENTS

| | | | |
|---|---|---|---|
| 8,835,346 B2 | 9/2014 | Gramiccioni et al. | |
| 2002/0136686 A1* | 9/2002 | Takahashi | B01J 23/60 423/651 |
| 2012/0136686 A1* | 5/2012 | Thompson | G06Q 10/063112 705/7.14 |

FOREIGN PATENT DOCUMENTS

| | | |
|---|---|---|
| CN | 102350347 A | 2/2012 |
| CN | 105597742 A | 5/2016 |

(Continued)

OTHER PUBLICATIONS

Matsumura et al., Surface properties of palladium supported on cerium oxide and its catalytic activity for methanol decomposition, Studies in Surface Science and Catalysis (130), 2000, 2315-2320).*

(Continued)

*Primary Examiner* — Jafar F Parsa
(74) *Attorney, Agent, or Firm* — Oblon, McClelland, Maier & Neustadt, L.L.P.

(57) ABSTRACT

Catalysts for hydrogenation of CO₂ to dimethyl ether. These catalysts comprise 0.1-10 wt % per total catalyst weight of a catalytic material containing Pd (e.g. metallic palladium), 0.05-5 wt % per total catalyst weight of a promoter containing Ca (e.g. metallic calcium), as well as 85-99 wt % of CeO₂ as a catalyst support. Methods of preparing and characterizing the catalysts as well as processes for catalyzing the hydrogenation of CO₂ to dimethyl ether and other byproducts such as methanol, carbon monoxide, and methane portrayed by reactant conversion, product selectivity, and catalyst stability are disclosed.

22 Claims, 4 Drawing Sheets

(51) Int. Cl.
   *B01J 35/02* (2006.01)
   *B01J 35/10* (2006.01)
   *C07C 41/01* (2006.01)
   *B01J 37/03* (2006.01)
   *B01J 37/02* (2006.01)
   *B01J 37/08* (2006.01)
   *B01J 37/18* (2006.01)
   *B01J 37/04* (2006.01)

(52) U.S. Cl.
   CPC ....... *B01J 35/1014* (2013.01); *B01J 37/0236* (2013.01); *B01J 37/036* (2013.01); *B01J 37/04* (2013.01); *B01J 37/08* (2013.01); *B01J 37/18* (2013.01); *C07C 41/01* (2013.01)

(58) Field of Classification Search
   CPC ........ B01J 35/1014; B01J 37/04; B01J 37/18; B01J 37/0236; B01J 37/036; B01J 23/10; C07C 41/01
   See application file for complete search history.

(56) References Cited

FOREIGN PATENT DOCUMENTS

JP          4159874 B2    10/2008
WO    WO 2009/053065 A1   4/2009

OTHER PUBLICATIONS

Ali Shan Malik, et al., "Development of highly selective PdZn/$CeO_2$ and Ca-doped PdZn/$CeO_2$ catalysts for methanol synthesis from $CO_2$ hydrogenation", Applied Catalysis A, General, vol. 560, 2018, pp. 42-53.

Ruizhi Chu, et al., "Catalytic kinetics of dimethyl ether one-step synthesis over $CeO_2$—CaO—Pd/HZSM-5 catalyst in sulfur-containing syngas process". Chinese Journal of Chemical Engineering, vol. 24, 2016, pp. 1735-1741.

Yunyun Zhou, "Nanostructured Cerium Oxide Based Catalysts: Synthesis, Physical Properties, and Catalytic Performance", Student Research Projects, Dissertations, and Theses—Chemistry Department, Aug. 2015, 212 pages.

Jian Sun. et al., "Catalysis Chemistry of Dimethyl Ether Synthesis", ACS Catalysis, vol. 4, 2014, pp. 3346-3356.

Rui-wen Liu, et al., "Synthesis of Dimethyl Ether from $CO_2$ and $H_2$ Using a Cu—Fe—Zr/HZSM-5 Catalyst System", Industrial & Engineering Chemistry Research, ACS Publications, vol. 52, 2013, pp. 16648-16655.

F. Frusteri, et al., "Multifunctionality of Cu—ZnO—$ZrO_2$/H-ZSM5 catalysts for the one-step $CO_2$-to-DME hydrogenation reaction", Applied Catalysis B: Environmental, vol. 162, 2015, pp. 57-65.

Xinhui Zhou, et al., "CuO—$Fe_2O_3$—$CeO_2$HZSM-5 bifunctional catalyst hydrogenated $CO_2$ for enhanced dimethyl ether synthesis", Chemical Engineering Science, vol. 153, 2016, pp. 10-20.

Oscar Oyola-Rivera, et al., "$CO_2$ hydrogenation to methanol and dimethyl ether by Pd—$Pd_2$Ga catalysts supported over $Ga_2O_3$ polymorphs". Journal of $CO_2$ Utilitzation, vol. 9, 2015, pp. 8-15.

Zu-zeng Qin, et al., "Hydrogenation of $CO_2$ to dimethyl ether on La-, Ce-modified Cu—Fe/HZSM-5 catalysts", Catalysis Communications, vol. 75, 2016, pp. 78-82.

Luyang Li, et al., "Facile preparation of highly efficient CuO—ZnO—$ZrO_2$/HZSM-5 bifunctional catalyst for one-step $CO_2$ hydrogenation to dimethyl ether: Influence of calcination temperature", Chemical Engineering Research and Design, vol. 111, 2016, pp. 100-108.

Sajo P.Naik, et al., "Synthesis of DME from $CO_2$/$H_2$ gas mixture", Chemical Engineering Journal, vol. 167, 2011, pp. 362-368.

G. Bonura, et al., "Hybrid Cu—ZnO—$ZrO_2$/H-ZSM5 system for the direct synthesis of DME by $CO_2$ hydrogenation", Applied Catalysis B: Environmental, vol. 140-141, 2013, pp. 16-24.

Gong-Xin Qi, et al., "DME synthesis from carbon dioxide and hydrogen over Cu—Mo/HZSM-5", Catalysis Letters, vol. 72, No. 1-2, 2001, pp. 121-124.

* cited by examiner

CERIA SUPPORTED PALLADIUM/CALCIUM CATALYST FOR HYDROGENATING CO₂ TO DIMETHYL ETHER

BACKGROUND OF THE INVENTION

Technical Field

The present disclosure relates to a catalyst containing palladium and calcium promoter supported on cerium oxide, methods of preparation, and processes of utilizing the catalyst in dimethyl ether production via $CO_2$ hydrogenation.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

$CO_2$ emissions are one of the major reasons for global warming and many technologies crucial to our society emit $CO_2$. Ways to mitigate deleterious human impact on the environment include $CO_2$ capture and development of non-$CO_2$ emitting technologies for energy generation and chemical production.

To meet the energy demand, anthropogenic activity using fossil fuels has caused an increased amount of $CO_2$ emission and has had a detrimental impact on the environmental system, i.e. global warming due to the greenhouse effect. Thus, the recycling of $CO_2$, and converting $CO_2$ to valuable products are urgently needed for the safety of our planet [Centi G, Quadrelli E A, Perathoner S. Catalysis for $CO_2$ conversion: a key technology for rapid introduction of renewable energy in the value chain of chemical industries. Energy & Environmental Science. 2013; 6(6):1711-31; and Olah G. A. Towards oil independence through renewable methanol chemistry. Angewandte Chemie International Edition. 2013; 52(1):104-7].

Dimethyl ether (DME) is one of the promising environmentally friendly alternatives to fossil fuels as it can be mixed with, or used in lieu of, LPG (liquid petroleum gas). DME can be used directly in slightly modified diesel engines. As a result of its high cetane number, DME gives low emissions of CO, NOx and particulates. Moreover, the bio-degradability, low toxicity and low corrosive activity make DME an attractive candidate for wide uses as a diesel fuel. In addition, DME can serve as an important intermediate chemical for the production of lower olefins, BTX aromatics, methyl acetate, and dimethyl sulfate, etc. [Bonura G, Cannilla C, Frusteri L, Mezzapica A, Frusteri F. DME production by $CO_2$ hydrogenation: Key factors affecting the behaviour of CuZnZr/ferrierite catalysts. Catalysis Today. 2017; 281:337-44, incorporated herein by reference in its entirety].

Currently, DME is produced from syngas (CO+H₂) via two different processes including (i) a two-step process, and (ii) a direct one-step synthesis. The two-step process is widely used in industry nowadays. In the first step, the syngas is converted to methanol over conventional copper-zinc-alumina based catalysts. In the second step, the methanol is dehydrated into DME over an acid catalyst such as $\gamma$-$Al_2O_3$ and ZSM-5 zeolite. A higher DME productivity may be achieved by the direct one-step synthesis, which circumvents thermodynamic limitations of methanol formation from syngas. However, a major obstacle for the wide application of this technology is the generation of a significant amount of $CO_2$, which substantially decreases the carbon efficiency of the process [Sun J, Yang G, Yoneyama Y, Tsubaki N. Catalysis chemistry of dimethyl ether synthesis. ACS Catalysis. 2014; 4(10):3346-56, incorporated herein by reference in its entirety].

The dehydration reaction of methanol to dimethyl ether (DME) (see equation 1) is often carried out over solid acid catalysts. In industry, $\gamma$-$Al_2O_3$ is used as a catalyst mostly.

This reaction is slightly exothermic in nature.

$$2CH_3OH_{(g)} \rightarrow CH_3OCH_{3(g)} + H_2O_{(g)} \quad \Delta H_{298\,K} = -23.4 \text{ kJ mol}^{-1} \quad (Eq. 1)$$

The direct hydrogenation of $CO_2$ to DME involves the application of bifunctional catalysts capable of simultaneously catalyzing two different reactions, with an overall stoichiometric equation given by equation (2)

$$2CO_{2(g)} + 6H_{2(g)} \rightarrow CH_3OCH_{3(g)} + 3H_2O_{(g)} \quad \Delta H_{298\,K} = -123.0 \text{ kJ mol}^{-1} \quad (Eq. 2)$$

This process involves steps of (i) methanol synthesis from $CO_2$ and $H_2$, and (ii) methanol dehydration. Often termed as "hybrid", the active elements of these bifunctional catalysts inherently include a component active in methanol synthesis, which is the preceding reaction in this process, while the methanol dehydration functionality of this hybrid tandem catalyst relies on the solid acid catalyst component such as $\gamma$-$Al_2O_3$ and H-ZSM-5. The use of hybrid catalysts was initially investigated and practiced for direct conversion of syngas to DME. Similar to the methanol synthesis reaction, the hybrid catalysts developed for the syngas-to-DME/gasoline conversion were also known to be active for $CO_2$ hydrogenation to DME.

The dual functions of a hybrid catalyst, namely, methanol synthesis and methanol dehydration, can be obtained in two different ways. The first approach is the preparation of a physical mixture where a methanol synthesis catalyst powder and a solid acid catalyst powder are simply mixed together mechanically, thus the functions of the two reactions are spatially well distributed. The second approach is the preparation of a chemical mixture where the catalytically active components for the two reactions are intentionally placed in close vicinity with the aim to facilitate the target synthesis of DME. For the first type of hybrid catalyst, the way in which the two separated components are located onto the catalytic reactor might have a substantial influence on the overall catalyst performance.

The development of new catalysts and processes for DME synthesis from $CO_2$ is urgently needed. Extensive studies of this topic have been carried out by many research groups and companies. A summary of the catalytic performance of recently reported DME catalysts can be found in Table 1.

TABLE 1

Catalytic activity and selectivity of existing DME catalysts

| Catalyst | Temp (°C.) | Pressure (MPa) | Gas hourly space velocity (GHSV) | ConV $CO_2$ % | Sel. DME % | Sel. CO % | Sel. $CH_3OH$ % | Ref.* |
|---|---|---|---|---|---|---|---|---|
| CuZnZr/FER | 260 | 5.0 | 8800 NL/kgcat/h $H_2:CO_2 = 5$ | 23.6 | 47.0 | 38.0 | 15.0 | [a] |
| CuO—$Fe_2O_3$—$ZrO_2$/H—ZSM-5 | 260 | 3.0 | 1500 mL/gcat/h $H_2:CO_2 = 5$ | 28.4 | 64.5 | 7.8 | 14.8 | [b] |
| Cu—ZnO—$ZrO_2$/HZSM-5 Multifunctional catalyst | 180 | 3.0 | 10,000 $h^{-1}$; $H_2:CO_2:N_2 = 9:3:1$ | 2.0 | 74.0 | 7.0 | 18.0 | [c] |
| CuO—$Fe_2O_3$—$CeO_2$HZSM-5 | 260 | 3.0 | 1,500 mL/gcat/$h^{-1}$ $H_2:CO_2 = 5$ | 20.9 | 63.1 | 22.7 | 7.0 | [d] |
| Pd—$Nb_2O_5$/LS—$Ga_2O_3$ | 270 | 1.7 | 27 $hr^{-1}$; $H_2:CO_2 = 6.4$ | 5.0 | 53.0 | 0 | 47.0 | [e] |
| Cu—Fe—Ce/H—ZSM5 | 260 | 3.0 | 1500 mL/gcat/hr; $H_2:CO_2 = 4$ | 18.1 | 52.0 | 25.4 | 2.1 | [f] |
| CuO—ZnO—$ZrO_2$/HZSM-5 (CZZH-300) One step synthesis | 250 | 3.0 | 2,500 $cm^3$/gm/hr; $H_2:CO_2 = 3$ | 22.2 | 67.6 | 23.8 | 8.6 | [g] |
| 6Cu)—3ZnO—1$Al_2O_3$/HZSM-5 | 260 | 5.0 | 3,000 $cm^3$/g/h; | 30.0 | 65.0 | 33.0 | 2.0 | [h] |
| Co—ZnO—ZrO2/HZSM-5 | 180 | 3.0 | 10000 $h^{-1}$ $H_2:CO_2:N_2 = 9:3:1$ | 1.9 | 75.3 | 8.1 | 16.6 | [i] |
| Cu—Mo/HSZSM-5 | 240 | 2.0 | 1,500 $h^{-1}$; $H_2:CO_2 = 3$ | 12.36 | 77,19 | 15.9 | 6.0 | [j] |

*Refs.
[a] Sun J, Yang G, Yoneyama Y, Tsubaki N. Catalysis chemistry of dimethyl ether synthesis. ACS Catalysis. 2014; 4(10):3346-56;
[b] Liu R-w, Qin Z-z, Ji H-b, Su T-m. Synthesis of dimethyl ether from $CO_2$ and $H_2$ using a Cu—Fe—Zr/HZSM-5 catalyst system. Industrial & Engineering Chemistry Research. 2013;52(47):16648-55;
[c]Frusteri F, Cordaro M, Camilla C, Bonura G. Multifunctionality of Cu-ZnO-$ZrO_2$/H-ZSM5 catalysts for the one-step $CO_2$-to-DME hydrogenation reaction. Applied Catalysis B: Environmental. 2015;162:57-65;
[d]Zhou X, Su T, Jiang Y, Qin Z, Ji H, Guo Z. CuO-$Fe_2O_3$-$CeO_2$ /HZSM-5 bifunctional catalyst hydrogenated $CO_2$ for enhanced dimethyl ether synthesis. Chemical Engineering Science. 2016;153:10-20;
[e]Oyola-Rivera O, Baltanás MA, Cardona-Martinez. N. $CO_2$ hydrogenation to methanol and dimethyl ether by Pd-$Pd_2$ Ga catalysts supported over $Ga_2$ $O_3$ polymorphs. Journal of $CO_2$ Utilization. 2015;9:8-15;
[f]Qin Z-z, Zhou X-h, Su T-m, Jiang Y-x, Ji H-b. Hydrogenation of $CO_2$ to dimethyl ether on La-, Ce-modified Cu-Fe/HZSM-5 catalysts. Catalysis Communications. 2016;75:78-82;
[g]Li L, Mao D Xiao J, Li L, Guo X, Yu J. Facile preparation of highly efficient CuO-ZnO-$ZrO_2$/HZSM-5 bifunctional catalyst for one-step $CO_2$ hydrogenation to dimethyl ether: Influence of calcination temperature. Chemical Engineering Research and Design. 2016;111:100-8;
[h]Naik SP, Ryu T, Bui V, Miller JD, Drinnan NB, Zmierczak W. Synthesis of DME from $CO_2/H_2$ gas mixture. Chemical engineering journal. 2011;167(1):362-8;
[i]Bonura G, Cordaro M, Spadaro L, Camilla C. Arena F, Frusteri F. Hybrid Cu-ZnO-$ZrO_2$/H-ZSM5 system for the direct synthesis of DME by $CO_2$ hydrogenation. Applied Catalysis B: Environmental. 2013;140:16-24; and
[j]Qi G-X, Fei J-H, Zheng X-M, Hou Z-Y. DME synthesis from carbon dioxide and hydrogen over Cu-Mo/HZSM-5. Catalysis letters. 2001; 72(1):121-4, each incorporated herein by reference in their entirety.

The process of dimethyl ether (DME) synthesis via hydrogenating $CO_2$ has a number of attractive features including: (i) the process will lead to decreased $CO_2$ emissions in the atmosphere as the feed gas is a mixture of $CO_2$ and $H_2$; (ii) the unreacted $CO_2$ can be recycled back to the reactor in the process, thus obtaining a high carbon efficiency; (iii) side products of the process such as $CH_3OH$ and CO are also valuable chemicals; and (iv) a possibility of using low pressure systems can be advantageous for commercial applications.

In view of the forgoing, one objective of the present disclosure is to provide $CeO_2$ supported palladium/calcium catalysts, a method of making the catalysts, and a process of using the catalysts in hydrogenating $CO_2$ for the synthesis of dimethyl ether. Such catalysts are highly active and selective for direct synthesis of DME from $CO_2$ hydrogenation. The activity and selectivity of the disclosed catalysts are far above the conventional hybrid catalyst currently being used for DME synthesis even at low pressure.

BRIEF SUMMARY OF THE INVENTION

According to a first aspect, the present disclosure relates to a $CeO_2$ supported palladium catalyst containing 0.05-5 wt % of a promoter including Ca, 0.1-10 wt % of a catalytic material including Pd, and 85-99 wt % of $CeO_2$, each relative to a total weight of the $CeO_2$ supported palladium catalyst, wherein the promoter and the catalytic material are deposited on the $CeO_2$.

In one embodiment, the promoter and the catalytic material are in the form of particles.

In one embodiment, the $CeO_2$ supported palladium catalyst has a surface area of 50-100 $m^2/g$.

In one embodiment, the $CeO_2$ supported palladium catalyst has an atomic ratio of palladium to calcium ranging from 1:50 to 75:1.

In one embodiment, the $CeO_2$ supported palladium catalyst has an atomic ratio of cerium to palladium ranging from 5:1 to 500:1.

According to a second embodiment, the present disclosure relates to a method of preparing the $CeO_2$ supported palladium catalyst of the first aspect. The method involves (i) heating an aqueous solution of a Ce(III) salt and citric acid to form a first mixture, (ii) mixing the first mixture with an aqueous solution of a Pd(II) salt and an aqueous solution of a Ca(II) salt to form a second mixture, (iii) heating the second mixture to form a gel, (iv) drying the gel to form a dried powder, (v) calcining the dried powder in air to form a pre-catalyst, and (vi) subjecting the pre-catalyst to $H_2$ gas thereby forming the $CeO_2$ supported palladium catalyst.

In one embodiment, a molar ratio of the citric acid to a total content of the Ce(III) salt and the Pd(II) salt ranges from 2:1 to 10:1.

In one embodiment, a molar ratio of the Pd(II) salt to the Ca(II) salt ranges from 1:50 to 75:1, and a molar ratio of the Ce(III) salt to the Pd(II) salt ranges from 5:1 to 500:1.

In one embodiment, the Ce(III) salt is cerium(III) nitrate.

In one embodiment, the Pd(II) salt is palladium(I) nitrate.

In one embodiment, the Ca(II) salt is calcium(II) nitrate.

According to a third aspect, the present disclosure relates to a process of producing dimethyl ether from $CO_2$ and $H_2$. The process involves contacting a stream containing $CO_2$ and $H_2$ with the $CeO_2$ supported palladium catalyst of the first aspect in a reactor, thereby producing dimethyl ether and at least one side product selected from the group consisting of methanol, carbon monoxide, and methane. A molar ratio of the $H_2$ to the $CO_2$ ranges from 1:1 to 6:1.

In one embodiment, the stream has a gas hourly space velocity of 1,800-12,000 mL/g·hr.

In one embodiment, the stream is contacted with the $CeO_2$ supported palladium catalyst at a temperature of 250-400° C.

In one embodiment, the stream is contacted with the $CeO_2$ supported palladium catalyst at a pressure of 1-30 bar.

In one embodiment, the stream further comprises an inert carrier gas.

In one embodiment, 7-80 mol % of the $CO_2$ present in the stream is converted to dimethyl ether and the at least one side product.

In one embodiment, a selectivity for dimethyl ether converted from the $CO_2$ ranges from 18-80%.

In one embodiment, a selectivity for carbon monoxide converted from the $CO_2$ is less than 22%, a selectivity for methane converted from the $CO_2$ is less than 20%, and a selectivity for methanol converted from the $CO_2$ is less than 30%.

In one embodiment, a conversion of $CO_2$ and a selectivity for dimethyl ether are maintained over a reaction period of 90 or more hours.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Embodiments of the present disclosure will now be described more fully hereinafter with reference to the accompanying drawings, in which some, but not all embodiments of the disclosure are shown.

The present disclosure may be better understood with reference to the following definitions. As used herein, the words "a" and "an" and the like carry the meaning of "one or more." Within the description of this disclosure, where a numerical limit or range is stated, the endpoints are included unless stated otherwise. Also, all values and subranges within a numerical limit or range are specifically included as if explicitly written out.

The present disclosure further includes all isotopes of atoms occurring in the present compounds. Isotopes include those atoms having the same atomic number but different mass numbers. By way of general example, and without limitation, isotopes of hydrogen include deuterium and tritium, and isotopes of oxygen include $^{16}O$, $^{7}O$, and $^{18}O$. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

As used herein, "compound" is intended to refer to a chemical entity, whether as a solid, liquid, or gas, and whether in a crude mixture or isolated and purified.

According to a first aspect, the present disclosure relates to a $CeO_2$ supported palladium catalyst, which comprises 0.05-5 wt % of a promoter comprising Ca, preferably 0.1-3 wt %, more preferably 0.15-1 wt % of the promoter comprising Ca; 0.1-10 wt % of a catalytic material comprising Pd, preferably 1-8 wt %, more preferably 3-6 wt % of the catalytic material comprising Pd; and 85-99 wt % of $CeO_2$, preferably 90-98 wt %, more preferably 95-97 wt % of $CeO_2$, each relative to a total weight of the $CeO_2$ supported palladium catalyst.

Palladium (Pd) in the form of Pd(0) and Pd(II) is widely used in organic synthesis including as a catalyst in C—C, C—N, and C—O bond formation. For example, palladium black is a coarse, sponge-like form of elemental palladium which is used in organic synthesis as a catalyst to accelerate hydrogenation reactions. Palladium on carbon (Pd/C), which has Pd metal supported on activated carbon, is a versatile catalyst used for catalytic hydrogenations and coupling reaction including Suzuki and Stille reactions. In one or more embodiments, the $CeO_2$ supported palladium catalyst comprises 0.1-10 wt % of metallic palladium by weight relative to a total weight of the $CeO_2$ supported palladium catalyst, preferably 0.5-9 wt %, preferably 1-8 wt %, preferably 2-7 wt %, preferably 3-6 wt %, preferably 4-5 wt % of metallic palladium by weight relative to a total weight of the $CeO_2$ supported palladium catalyst. In certain embodiments, other palladium species including Pd(II) (e.g. PdO) and/or Pd(IV) (e.g. $PdO_2$) may present in the $CeO_2$ supported palladium catalyst in addition to, or in lieu of metallic palladium.

As used herein, a promoter refers to an additive intended to improve catalyst performance. In one or more embodiments, the $CeO_2$ supported palladium catalyst comprises metallic calcium as a promoter. Metal promoters such as calcium may function to increase the dispersion of palladium on support surface. Furthermore, the addition of calcium promoters to the $CeO_2$ supported palladium catalyst may block acid sites and thus decreases the total acidity of the catalyst. In a preferred embodiment, the $CeO_2$ supported palladium catalyst comprises 0.05-5 wt % of metallic calcium by weight relative to a total weight of the $CeO_2$ supported palladium catalyst, preferably 0.1-4 wt %, preferably 0.15-3 wt %, preferably 0.3-2.5 wt %, preferably 0.5-2 wt %, preferably 1-1.5 wt % of metallic calcium by weight relative to the total weight of the $CeO_2$ supported palladium catalyst. In certain embodiments, other calcium species including Ca(II) (e.g. CaO, $Ca(OH)_2$, $CaCO_3$) may present in the $CeO_2$ supported palladium catalyst in addition to, or in lieu of metallic calcium.

It is equally envisaged that the $CeO_2$ supported palladium catalyst of the present disclosure may be adapted to incorporate other promoters in addition to Ca. Preferably, alkaline earth metals such as magnesium (Mg), strontium (Sr), and barium (Ba) may be used herein as additional promoters. Other exemplary promoters include, but are not limited to, metallic promoters (e.g. Cr, Mo, Ta, W), alkali promoters (e.g. Li, K, Rb), and halide promoters (e.g. Cl).

As used herein, a catalyst support material refers to a material, usually a solid with a high surface area, to which a catalyst is affixed. The reactivity of heterogeneous catalyst and nanomaterial based catalysts occurs at the surface atoms. Thus, great effort is made herein to maximize the surface of a catalyst by distributing it over the support. The support may be inert or participate in the catalytic reactions. The support materials used in catalyst preparation play a role in determining the physical characteristics and performance of the catalysts. Conventional supports include various kinds of carbon, alumina, and silica. In a preferred embodiment, $CeO_2$ serves as a catalyst support material in the presently disclosed $CeO_2$ supported palladium catalyst.

Cerium(IV) oxide ($CeO_2$), also known as ceria, ceric oxide, ceric dioxide, cerium oxide or cerium dioxide, is an oxide of the rare-earth metal cerium. Cerium(IV) oxide may be formed by the calcination of cerium oxalate or cerium hydroxide. Cerium(III) oxide, which is less stable, can be oxidized and form cerium(IV) oxide. Cerium oxide adopts the fluorite structure; however it releases oxygen at high temperatures to give a non-stoichiometric, anion deficient form that retains the fluorite lattice. In a preferred embodiment, the $CeO_2$ supported palladium catalyst of the present disclosure comprises 85-99 wt % of $CeO_2$ by weight relative to a total weight of the $CeO_2$ supported palladium catalyst, preferably 88-98 wt %, preferably 90-97 wt %, preferably 92-96 wt %, preferably 93-95 wt % of $CeO_2$ by weight relative to a total weight of the $CeO_2$ supported palladium catalyst.

It is equally envisaged that the $CeO_2$ supported palladium catalyst of the present disclosure may be adapted to incorporate other catalyst support materials in addition to $CeO_2$. These catalyst support materials include, but are not limited to, $ZrO_2$, $TiO_2$, $SiO_2$, $NbO_5$, MgO, $Al_2O_3$, and zeolites.

In one or more embodiments, the $CeO_2$ supported palladium catalyst of the present disclosure has an atomic ratio of palladium to calcium ranging from 1:50 to 75:1, from 1:40 to 70:1, from 1:30 to 60:1, from 1:20 to 50:1, from 1:10 to 40:1, from 1:1 to 35:1, from 2:1 to 30:1, from 4:1 to 25:1, from 5:1 to 20:1, from 6:1 to 18:1, from 7:1 to 16:1, from 8:1 to 14:1, from 9:1 to 12:1, or about 10:1. In one or more embodiments, the $CeO_2$ supported palladium catalyst has an atomic ratio of cerium to palladium ranging from 5:1 to 500:1, from 6:1 to 400:1, from 7:1 to 300:1, from 8:1 to 200:1, from 9:1 to 100:1, from 10:1 to 50:1, from 11:1 to 25:1, from 12:1 to 20:1, from 13:1 to 18:1, from 14:1 to 16:1, or about 15:1.

In one or more embodiments, the promoter and the catalytic material are in the form of particles. In a preferred embodiment, the promoter comprising Ca is in the form of nanoparticles having particle diameters of 1-100 nm, 2-50 nm, 4-25 nm, or 5-10 nm. In another preferred embodiment, the catalytic material comprising Pd is in the form of nanoparticles having particle diameters of 1-100 nm, 2-50 nm, 4-25 nm, or 5-10 nm.

In one or more embodiments, the aforementioned promoter and catalytic material are deposited on a catalytic support material, e.g. $CeO_2$. In a preferred embodiment, the catalytic material comprising metallic palladium and promoter comprising metallic calcium are deposited on a catalyst support material, e.g. $CeO_2$. As used herein, "deposited on" describes the catalytic materials being disposed on or impregnated in a support material such that the support material is completely or partially filled throughout, saturated, permeated, and/or infused with the catalytic materials. The catalytic materials and promoters may be affixed to $CeO_2$ in any reasonable manner, such as physisorption, chemisorption, or mixtures thereof. In a related embodiment, the $CeO_2$ supported palladium catalyst of the present disclosure may have a catalyst support $CeO_2$ with both metallic calcium and metallic palladium decorated on the surface of the $CeO_2$. In another related embodiment, the $CeO_2$ supported palladium catalyst may have a catalyst support $CeO_2$ with both metallic calcium and metallic palladium disposed on the surface and impregnated in the $CeO_2$. In preferred embodiments, the metallic calcium and metallic palladium are homogeneously dispersed in the $CeO_2$ support.

In one embodiment, the metallic calcium is affixed to one or more surfaces of the metallic palladium in the $CeO_2$ supported palladium catalyst. These materials may be affixed via strong atomic bonds (e.g. metallic, ionic, and covalent bonds) and/or weak interactions such as van der Waals, or hydrogen bonds. In one embodiment, the metallic calcium and metallic palladium are present in the form of a PdCa alloy. For example, the $CeO_2$ supported palladium catalyst may comprise PdCa alloys having metallic calcium embedded between palladium atoms to become integral with the lattice structure of the metallic palladium. Alternatively, the metallic calcium may be embedded into the pores of the palladium lattice and thus not integral to the palladium lattice. In certain alternative embodiments, the metallic calcium and/or metallic palladium is not incorporated into the lattice structure of metallic palladium and/or metallic calcium and may be adsorbed on the surface (e.g. by van der Waals and/or electrostatic forces) of the metallic palladium and/or metallic calcium.

In one embodiment, greater than 10% of the surface area (i.e. surface and pore spaces) of the support material (e.g. $CeO_2$) is covered by the catalytic material and the promoter (e.g. metallic palladium and metallic calcium), preferably greater than 15%, preferably greater than 20%, preferably greater than 25%, preferably greater than 30%, preferably greater than 35%, preferably greater than 40%, preferably greater than 45%, preferably greater than 50%, preferably greater than 55%, preferably greater than 60%, preferably greater than 65%, preferably greater than 70%, preferably greater than 75%, preferably greater than 80%, preferably greater than 85%, preferably greater than 90%, preferably greater than 95%, preferably greater than 96%, preferably greater than 97%, preferably greater than 98%, preferably greater than 99% of $CeO_2$ support is covered by the catalytic material and the promoter.

In one embodiment, the $CeO_2$ supported palladium catalyst is in the form of particles with diameters of 4-10 μm, 4.5-9.5 μm, 5-9 μm, 5.5-8.5 μm, 6-8 μm, or 6.5-7.5 μm. In one or more embodiments, the $CeO_2$ supported palladium catalyst has a surface area of 25-200 m$^2$/g, preferably 40-150 m$^2$/g, preferably 50-120 m$^2$/g, preferably 55-100 m$^2$/g, preferably 60-90 m$^2$/g, preferably 70-80 m$^2$/g. The Brunauer-Emmet-Teller (BET) theory (S. Brunauer, P. H. Emmett, E. Teller, *J. Am. Chem. Soc.* 1938, 60, 309-319, incorporated herein by reference) aims to explain the physical adsorption of gas molecules on a solid surface and serves as the basis for an important analysis technique for the measurement of a specific surface area of a material. Specific surface area is a property of solids which is the total surface area of a material per unit of mass, solid or bulk volume, or cross sectional area. In most embodiments, pore volume and BET surface area are measured by gas adsorption analysis, preferably $N_2$ adsorption analysis. In one embodiment, the surface area of the $CeO_2$ supported palladium catalyst is determined by BET analysis via $N_2$ adsorption isotherms.

According to a second embodiment, the present disclosure relates to a method of preparing the $CeO_2$ supported palladium catalyst of the first aspect. The method involves (i) beating an aqueous solution of a Ce(III) salt and citric acid to form a first mixture, (ii) mixing the first mixture with an aqueous solution of a Pd(II) salt and an aqueous solution of a Ca(II) salt to form a second mixture, (iii) heating the second mixture to form a gel, (iv) drying the gel to form a dried powder, (v) calcining the dried powder in air to form a pre-catalyst, and (vi) subjecting the pre-catalyst to $H_2$ gas, thereby forming the $CeO_2$ supported palladium catalyst.

As used herein, a salt refers to an ionic compound resulting from the neutralization reaction of an acid and a base. Salts are composed of related numbers of cation (positively charged ions) and anions (negatively charged ions) such that the product is electrically neutral (without a net charge). These component ions may be inorganic (e.g. chloride, $Cl^-$) or organic (e.g. acetate, $CH_3CO_2^-$) and may be monoatomic (e.g. fluoride, $F^-$) or polyatomic (e.g. sulfate, $SO_4^{2-}$). Exemplary conventional salts include, but are not limited to, those derived from inorganic acids including, but not limited to, hydrochloric, hydrobromic, sulfuric, sulfamic, phosphoric, and nitric; and those derived from organic acids including, but not limited to, acetic, propionic, succinic, glycolic, stearic, lactic, malic, tartaric, citric, ascorbic, pamoic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isethionic, and mixtures and hydrates thereof and the like. The present disclosure includes all hydration states of a given salt or formula, unless otherwise noted. For example, $Ca(NO_3)_2$ includes anhydrous $Ca(NO_3)_2$, tetrahydrate $Ca(NO_3)_2.4H_2O$, and any other hydrated forms or mixtures. $Ce(NO_3)_3$ includes anhydrous $Ce(NO_3)_2$, hexahydrate $Ce(NO_3)_3.6H_2O$, and any other hydrated forms or mixtures.

Exemplary suitable Ce(III) salts include, but are not limited to, cerium(III) nitrate, cerium(III) nitrate hexahydrate, cerium(III) sulfate, cerium(III) sulfate octahydrate, cerium(III) oxalate hydrate, cerium(III) carbonate hydrate, cerium(III) hydroxide, cerium(III) fluoride anhydrous, cerium(II) chloride anhydrous, cerium(III) bromide anhydrous, and cerium(III) iodide anhydrous. Preferably, the Ce(III) salt is cerium(III) nitrate. In certain embodiments, Ce(IV) salts such as cerium(IV) hydroxide, cerium(IV) sulfate hydrate, and ammonium cerium(IV) nitrate may be used in addition to or in lieu of the Ce(III) salt.

The presently disclosed $CeO_2$ supported palladium catalyst may be prepared via solid-state chemistry, solution techniques including co-precipitation, hydrothermal processing, solvothermal methods, and sol-gel chemistry. Sol-gel chemistry may provide a homogeneous mixing of precursors on the atomic level, thus enable a greater control over particle morphology and size at lower processing temperatures and shorter reaction times. Preferably, sol-gel chemistry is used for the preparation of the $CeO_2$ supported palladium catalyst.

Citric acid is a weak triprotic acid that has the chemical formula $C_6H_8O_7$. Citric acid is an effective chelating agent useful for sol-gel processes. With three carboxylate groups, citrate ions may form complexes with metallic cations. Other chelating agents useful for the present disclosure that may be used in addition to, or in lieu of citric acid include, but are not limited to, ethylenediaminetetraacetic acid (EDTA), oxalic acid, malic acid, sebacic acid, tartaric acid, glucose, amino acids such as glutamine and histidine, as well as other triprotic acids such as isocitric acid, aconitic acid, and propane-1,2,3-tricarboxylic acid.

In one embodiment, the Ce(II) salt is present in the aqueous solution of the Ce(III) salt and citric acid at a concentration of 0.05-1 M, preferably 0.1-0.5 M, more preferably 0.2-0.3 M. In one embodiment, the citric acid is present in the aqueous solution of the Ce(III) salt and citric acid at a concentration of 0.15-3 M, preferably 0.3-1.5 M, more preferably 0.6-1 M. In one step of the method, the aqueous solution of the Ce(III) salt and citric acid is heated at a temperature of 30-70° C., preferably 40-60° C., more preferably 45-55° C., or about 50° C. for 0.1-2 hours, 0.2-1 hour, or 0.3-0.5 hour to form a first mixture.

In one step of the method, the first mixture is mixed with an aqueous solution of a Pd(II) salt and an aqueous solution of a Ca(I) salt to form a second mixture. Exemplary suitable Pd(II) salts include, but are not limited to, palladium(II) nitrate, palladium(II) nitrate hydrate, palladium(II) acetate, palladium(II) chloride, palladium(II) bromide, palladium(II)

iodide, palladium(II) sulfate, tetraamminepalladium(II) chloride monohydrate, and tetraamminepalladium(II) bromide. Preferably, the Pd(II) salt is palladium(II) nitrate. In one embodiment, the Pd(II) salt is present in the second mixture at a concentration of 1-50 mM, 2-25 mM, 4-15 mM, or 5-10 mM. Exemplary suitable Ca(II) salts include, but are not limited to, calcium(II) nitrate, calcium(II) nitrate tetrahydrate, calcium(II) chloride dehydrate, calcium(II) bromide, calcium(II) iodide, calcium(II) sulfate dehydrate, calcium(II) sulfate dehydrate, calcium(II) carbonate, calcium(I) acetate, calcium(II) hydroxide, calcium(II) nitrite, and calcium(II) oxalate hydrate. Preferably, the Ca(II) salt is calcium(II) nitrate. In one embodiment, the Ca(II) salt is present in the second mixture at a concentration of 0.1-5 mM, 0.2-2.5 mM, 0.4-1.5 mM, or 0.5-1 mM. In one or more embodiments, a molar ratio of the citric acid to a total content of the Ce(III) salt and the Pd(II) salt in the second mixture ranges from 2:1 to 10:1, 2.2:1 to 8:1, 2.4:1 to 6:1, 2.6:1 to 4:1, 2.8:1 to 3.5:1, or about 3:1.

In a preferred embodiment, a molar ratio of the Pd(II) salt to the Ca(II) salt in the second mixture ranges from 1:50 to 75:1, 1:25 to 50:1, 1:10 to 40:1, 1:1 to 30:1, 5:1 to 20:1, or about 10:1. In another preferred embodiment, a molar ratio of the Ce(III) salt to the Pd(II) salt in the second mixture ranges from 5:1 to 500:1, 6:1 to 250:1, 7:1 to 100:1, 8:1 to 80:1, 9:1 to 60:1, 10:1 to 40:1, 11:1 to 30:1, 12:1 to 25:1, 13:1 to 20:1, 14:1 to 18:1, or about 15:1.

In one step of the method, the second mixture is heated at a temperature of 70-110° C., preferably 80-100° C., more preferably 85-95° C., or about 90° C. for 6-48 hours, 8-24 hours, 10-18 hours, or 12-16 hours to form a gel. The heating of the second mixture may be performed using a hot plate (e.g. an electrically driven heating plate), a water bath, or an oven. In certain embodiments, the second mixture may be stirred (e.g. at a speed of 50-1000 rpm, 50-900 rpm, 50-700 rpm, 50-500 rpm, 100-500 rpm, or 200-400 rpm), or in certain embodiments the second mixture may be left to stand or not agitated during the heating.

The gel collected may be dried in an oven at a temperature of 100-180° C., 105-160° C., 110-140° C., or 120-130° C. for 8-36 hours, 12-24 hours, 16-20 hours, or about 18 hours to form a dried powder. The dried powder may then be calcined at 250-650° C., preferably 300-600° C., preferably 350-550° C., preferably 400-500° C. for 0.5-8 hours, 1-6 hours, 2-5 hours, or 3-4 hours to form the pre-catalyst. In a preferred embodiment, the dried powder is calcined in air to form the pre-catalyst. The air may be provided in the form of an air flow comprising 15-30 mol % $O_2$, preferably 20-25 mol % $O_2$, preferably 20.5-22 mol % $O_2$, or about 21 mol % $O_2$ at a molar percentage and 70-80 mol % $N_2$, preferably 77-79 mol % $N_2$, or about 78 mol % $N_2$. In one embodiment, the pre-catalyst formed herein comprises calcium species including Ca(II) (e.g. CaO, Ca(OH)$_2$, CaCO$_3$). In another embodiment, the pre-catalyst formed herein comprises palladium species such as Pd(II) (e.g. PdO) and/or Pd(IV) (e.g. PdO$_2$).

As used herein, reduction refers to the gain of electrons or a decrease in oxidation state by a molecule, atom or ion. In one embodiment, reduction of the pre-catalyst to form the $CeO_2$ supported palladium catalyst is performed by subjecting the pre-catalyst to $H_2$ gas. In a preferred embodiment, the pre-catalyst is subjected to a flow of hydrogen gas comprising 75-100% $H_2$, 90-99.9% $H_2$, or 95-99% $H_2$ as a molar percentage at a flow rate of 5-100 cm$^3$/min, preferably 10-75 cm$^3$/min, more preferably 15-50 cm$^3$/min, or about 20 cm$^3$/min. In a preferred embodiment, the reduction of the pre-catalyst under hydrogen gas flow is performed at a temperature of 400-800° C., preferably 450-700° C., preferably 500-650° C., preferably 525-600° C., or about 550° C., a pressure of 0.5-4 atm, 0.75-2 atm, or about 1 atm for a period of 0.25-8 hours, preferably 0.5-6 hours, preferably 0.75-4 hours, preferably 1-2 hours. In one embodiment, at least a portion of calcium species including Ca(II) (e.g. CaO, Ca(OH)$_2$, CaCO$_3$) that may present in the pre-catalyst are reduced to metallic calcium after the reduction of the pre-catalyst. In preferred embodiment, 50-99%, 60-95%, 75-90%, or 80-85% as a molar percentage of calcium species including Ca(II) (e.g. CaO, Ca(OH)$_2$, CaCO$_3$) that may present in the pre-catalyst are reduced to metallic calcium after the reduction of the pre-catalyst. In related embodiments, the reduction of the pre-catalyst may generate metallic palladium from palladium species including Pd(II) (e.g. PdO) and/or Pd(IV) (e.g. PdO$_2$) that may present in the pre-catalyst. Alternatively, the reduction step of the pre-catalyst may occur prior to using the $CeO_2$ supported palladium catalyst in catalytic process of producing dimethyl ether from $CO_2$ discussed hereinafter.

In one embodiment, the $CeO_2$ supported palladium catalyst is further pelletized and ground to produce the catalyst pellets of desired shapes. The pelletizing may be done with a rotary drum pelletizer, a pan pelletizer, or a pellet press and the calcined powder may be subjected to a pressure of 50-6,000 psi, 100-5,000 psi, or 500-3,000 psi. The pellets may be in a prismatic shape, such as a cylinder or a rectangular prism, though in other embodiments, the catalyst pellets may be formed into spherical or hemispherical shapes.

According to a third aspect, the present disclosure relates to a process of producing dimethyl ether from $CO_2$ and $H_2$. The process involves contacting a stream containing $CO_2$ and $H_2$ with the $CeO_2$ supported palladium catalyst of the first aspect in a reactor, thereby producing dimethyl ether and at least one side product selected from the group consisting of methanol, carbon monoxide, and methane.

In one or more embodiments, the stream is fed to the reactor at a gas hourly space velocity (GHSV) of 1,800-12,000 mL/g·hr, preferably 2,500-10,000 mL/g·hr, more preferably 6,000-9,000 mL/g·hr. In preferred embodiments, the stream has a molar ratio of the $H_2$ to the $CO_2$ ranges from 1:1 to 6:1, preferably from 2:1 to 5:1, more preferably from 2.5:1 to 4:1, or about 3:1. In one embodiment, the stream further comprises an inert carrier gas. The inert gas may present at a concentration of 50-85 vol %, 60-80 vol %, or 65-75 vol % relative to a total volume of the stream. Preferably, the inert gas is helium, argon, or nitrogen. Most preferably, the inert gas is argon. In other embodiments, the inert gas may be any gas that is not reacted or converted, and preferably does not affect the catalytic process beyond changing flowrates or concentrations. In an alternative embodiment, the stream fed to the reactor consists of only $CO_2$ and $H_2$.

The reactor may be a fixed-bed reactor or a fluidized bed reactor. In at least one embodiment, the reactor is the Microactivity (MA) Effi reactor (PID Eng & Tech, Spain). In one embodiment, the dimension of the reactor paraller with the stream flow has a length of 5 mm-5 cm, preferably 6 mm-2 cm, more preferably 7 mm-12 mm. In one embodiment, the $CeO_2$ supported palladium catalyst may sit on or be attached to a solid support, such as the interior of a tubing, on or inside a porous glass frit or quartz filter disc, or on a quartz or silicon wafer. In a related alternative embodiment, a fluidized bed reactor may be used with loose $CeO_2$ supported palladium catalyst instead of a fixed bed reactor.

Prior to the reaction, the rector may be heated to a reaction temperature of 250-400° C., preferably 270-380° C., preferably 300-360° C., preferably 320-340° C. The reactor may reach this reaction temperature by increasing its internal temperature at a rate of 2-10° C./min, preferably 3-8° C./min, more preferably 4-6° C. In one or more embodiments, the aforementioned reduction step of the pre-catalyst may occur prior to the catalytic process to generate the $CeO_2$ supported palladium catalyst. In one or more embodiments, the stream is contacted with the $CeO_2$ supported palladium catalyst at the reaction temperature of 250-400° C., preferably 270-380° C., preferably 300-360° C., preferably 320-340° C. In one embodiment, the stream is contacted with the $CeO_2$ supported palladium catalyst at a pressure of 1-30 bar, 2-25 bar, 3-20 bar, 4-15 bar, 5-10 bar, or 6-8 bar.

Contacting the stream with the $CeO_2$ supported palladium catalyst disclosed herein in any of its embodiments may result in a conversion of the $H_2$ and $CO_2$ reactants into gas phase products such as dimethyl ether (DME) and at least one side product selected from the group consisting of methanol, carbon monoxide, and methane. The flow of the stream allows the displacement of the gas phase products and unconverted $H_2$ and $CO_2$. These species can then be separated by one or more molecular sieves, adsorbents, or trapping agents and analyzed to determine concentrations. The molecular sieve, adsorbent, or trapping agent may be carbon based adsorbents, such as activated carbon, charcoal, or the Carbopak® series, porous polymers, such as the Chromosorb® series, the Porapak® series, the Tenax® series, the HayeSep® series (e.g. HayeSep Q packed colume), the XAD® series, clays, diatomaceous earth, magnesium silicates, such as Florisil®, ashes, micronized silicon dioxide, christobalite, hydrated sodium calcium aluminosilicates, chitosan, granulas, anionic ion exchange resins, cationic ion exchange resins, modified ion exchange resins, zeolites, perlite, bentonite, C4-30 aliphatic hydrocarbons, C4-30 unsaturated hydrocarbons, gas chromatography stationary phases, liquid chromatography stationary phases, polyethylene glycol with a melting point in the range from 30 to 100° C., preferably 40 to 50° C., silica gel, aluminum oxide, cellulose, granulates, high boiling liquids such as polysiloxanes, phenyl substituted stationary phases, bases, acids, and diethylene glycol succinate derivatives. The powder forms of molecular sieves may be of type 3A, 4A, 5A, and 13X. Following separation, a GC, such as an Agilent 7890 A, and/or a mass spectrometer may be used to determine concentrations. Alternatively, a GC-MS may be used without a molecular sieve or without prior separation of the products. In an alternative embodiment, the exit gas stream may be condensed to form a liquid mixture, which is then analyzed. In one embodiment, before the exit gas stream is analyzed, the reaction may be allowed to run for 1-6 h, preferably 2-4 h, more preferably 2.5-3.5 h at specific reaction conditions so that the reaction products achieve steady state concentrations.

In other embodiments, a distillation column or distillation tower may be used to separate or purify DME. The distillation column may be a fractionating column, and the distillation column may be used in a continuous or batch distillation process. Other separation processes may be used, such as fractional freezing.

The success of the reaction may be determined by the percent conversion of the reactants, the percent selectivity of the gas phase products, and/or the percent yield of the gas phase products. Based on these values, a person having ordinary skill in the art may be able to determine preferable reaction parameters such as reaction temperature, pressure, and GHSV.

As used herein, the percent conversion of a reactant is a mol % of the reactant converted into one or more products, relative to a total amount of the reactant fed to the reactor. This may be determined by subtracting the unreacted amount of the reactant (e.g. $CO_{2\ out}$) from the total amount of the reactant fed (e.g. $CO_{2\ in}$), dividing by the total amount of the reactant fed, and converting to a percentage. The percentage conversion for $CO_2$ is then:

$$CO_2 \text{ conversion } (\%) = \frac{(\text{mol } CO_{2\ in} - \text{mol } CO_{2\ out}) \times 100}{\text{mol } CO_{2\ in}}$$

Figure 1:
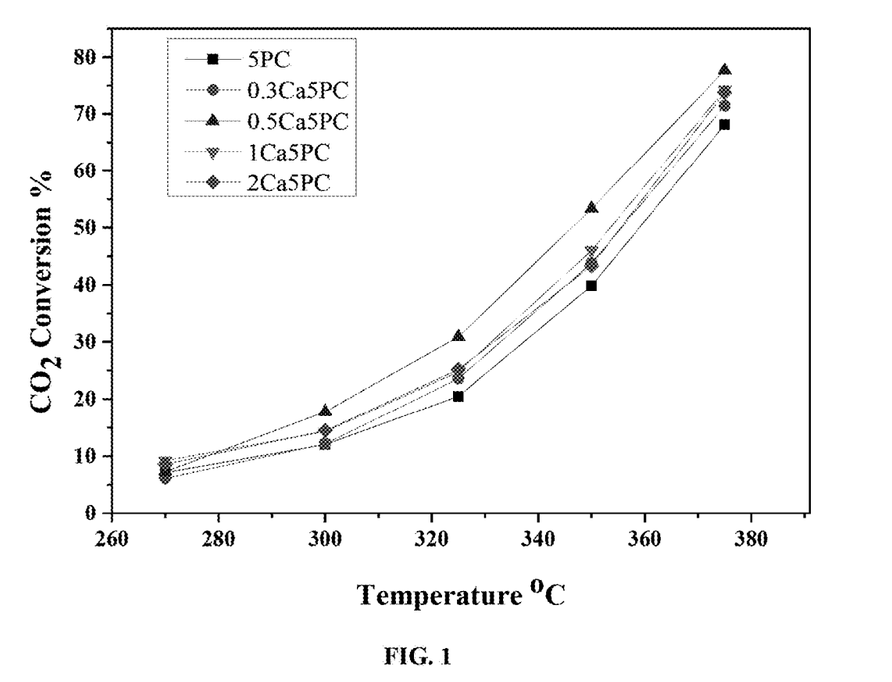
FIG. 1 shows $CO_2$ conversions of DME synthesis catalyzed by 5% Pd/$CeO_2$ (5PC), 0.3% Ca5% Pd/$CeO_2$ (0.3Ca5PC), 0.5% Ca5% Pd/$CeO_2$ (0.5Ca5PC), 1% Ca5% Pd/$CeO_2$ (1Ca5PC), and 2% Ca5% Pd/$CeO_2$ (2Ca5PC), respectively, at an operating pressure of 30 bar, a gas hourly space velocity (GHSV) of 2400 mL/g·hr, and over a temperature range of 260-380° C.
Figure 2:
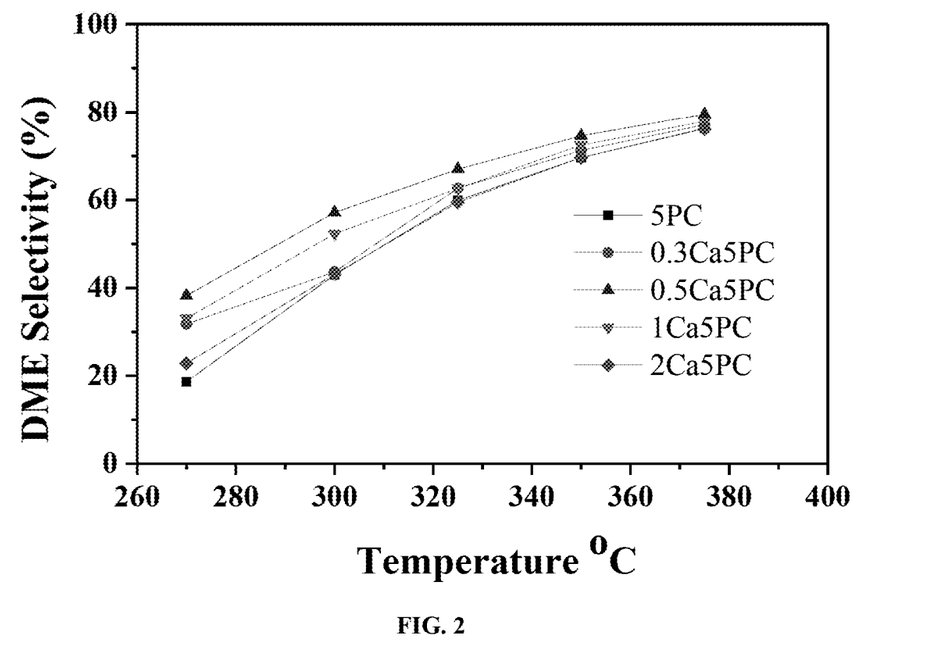
FIG. 2 shows product selectivities of DME synthesis catalyzed by 5% Pd/$CeO_2$ (5PC), 0.3% Ca5% Pd/$CeO_2$ (0.3Ca5PC), 0.5% Ca5% Pd/$CeO_2$ (0.5Ca5PC), 1% Ca5% Pd/$CeO_2$ (1Ca5PC), and 2% Ca5% Pd/$CeO_2$ (2Ca5PC), respectively, at an operating pressure of 30 bar, and a GHSV of 2400 mL/g·hr, over a temperature range of 260-380° C.
Figure 3:
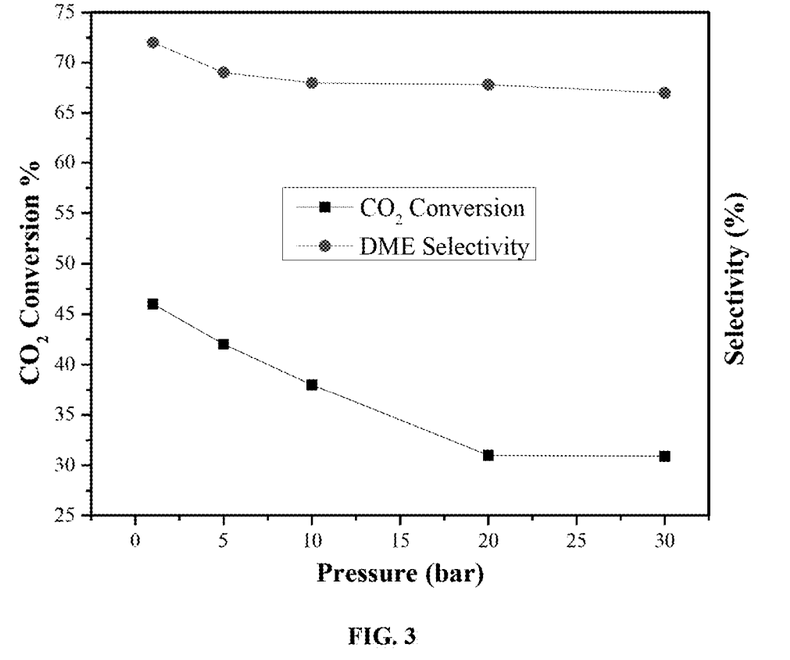
FIG. 3 shows $CO_2$ conversions and product selectivities of DME synthesis catalyzed by 0.5% Ca5% Pd/$CeO_2$ at a GHSV of 2400 mL/g·hr, and a temperature of 325° C., over an operating pressure range of 1-30 bar.
Figure 5:
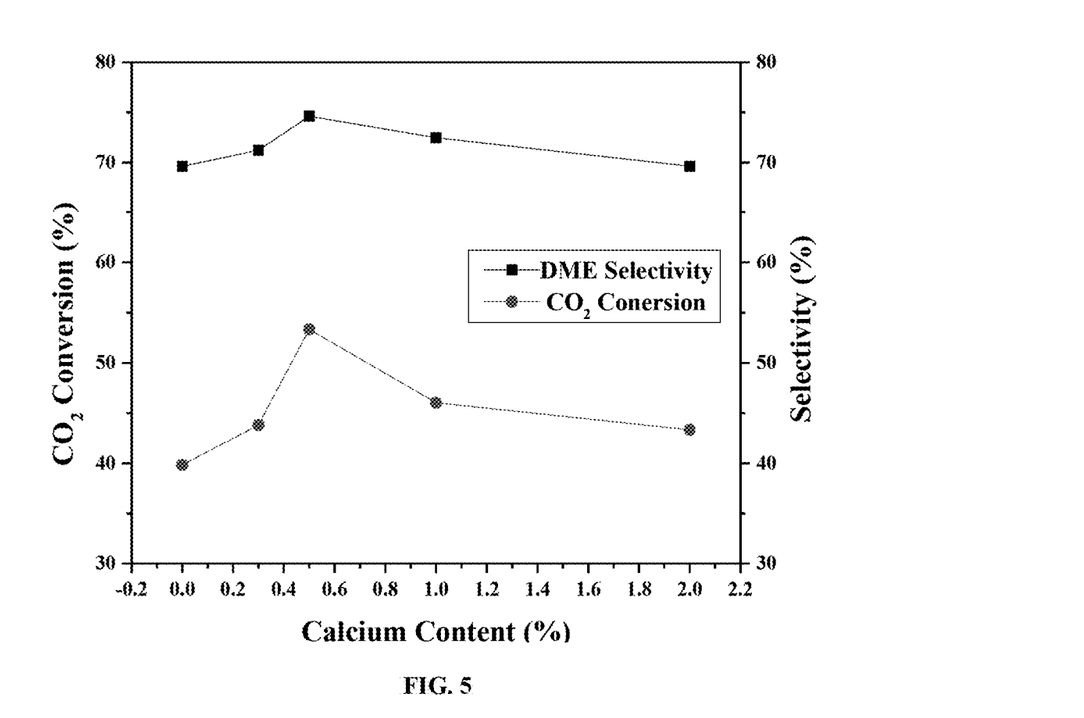
FIG. 5 summarizes the promotion effect of calcium content in catalysts on $CO_2$ conversions and product selectivities of DME synthesis at a temperature of 350° C., an operating pressure of 30 bar, and a GHSV of 2400 mL/g·hr.
Figure 6:
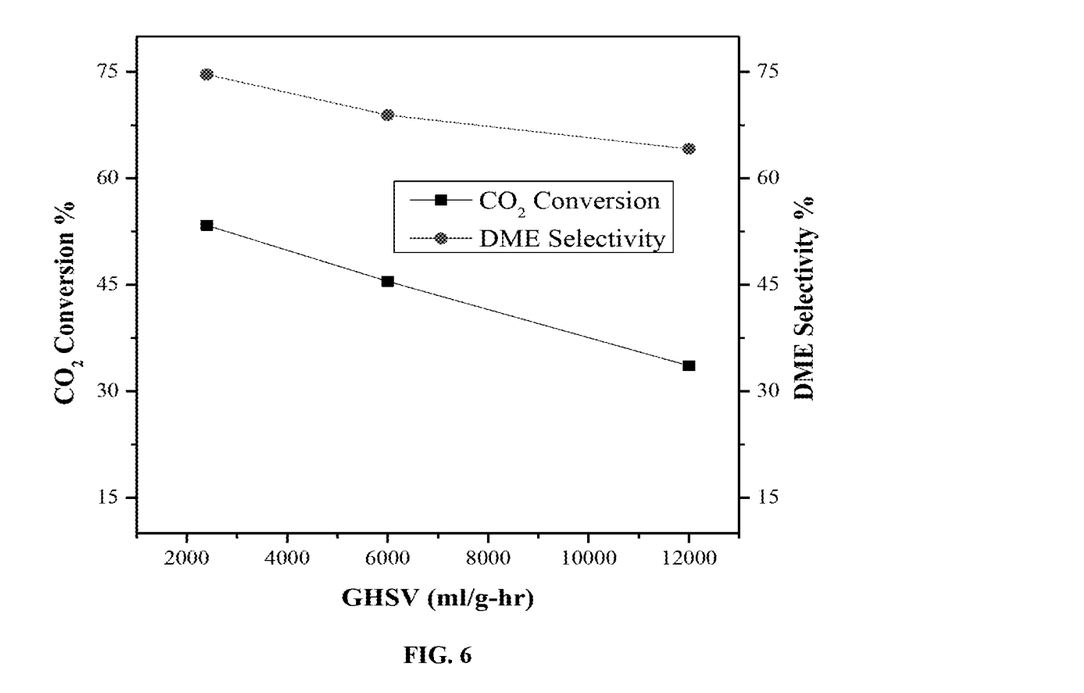
FIG. 6 depicts the effect of varying GHSV on $CO_2$ conversions and product selectivities of DME synthesis catalyzed by 0.5% Ca5% Pd/$CeO_2$ at a temperature of 350° C., and an operating pressure of 30 bar.
Figure 7:
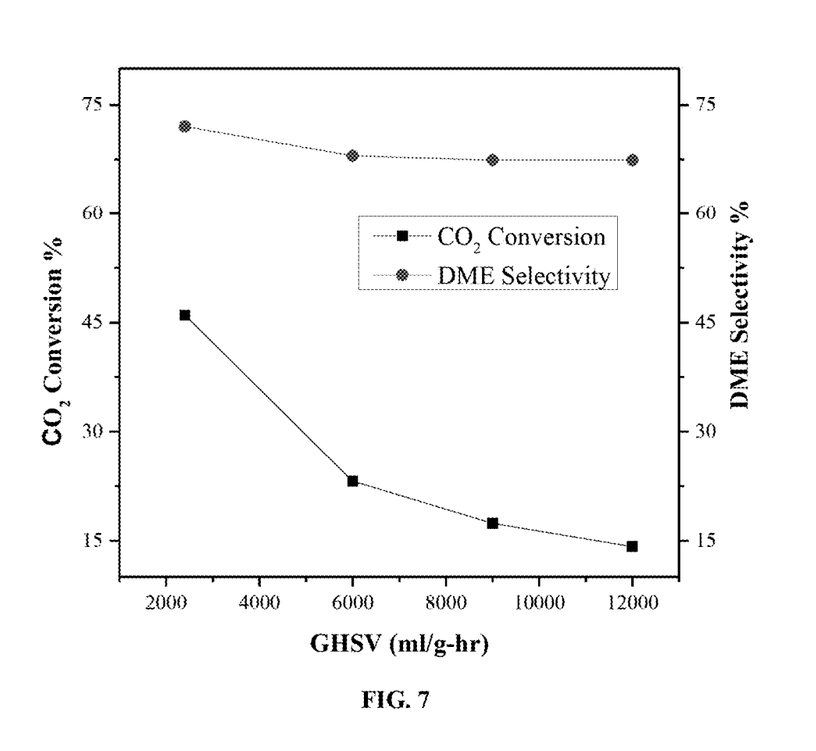
FIG. 7 depicts the effect of varying GHSV on $CO_2$ conversions and product selectivities of DME synthesis catalyzed by 0.5% Ca5% Pd/$CeO_2$ at a temperature of 350° C., and an operating pressure of 1 bar.

FIGS. 1, 3, 5, 6, and 7, and Tables 2 and 3 show example conversion percentages of $CO_2$ using the $CeO_2$ supported palladium catalysts including 0.3% Ca5% Pd/$CeO_2$ (0.3Ca5PC), 0.5% Ca5% Pd/$CeO_2$ (0.5Ca5PC), 1% Ca5% Pd/$CeO_2$ (1Ca5PC), and 2% Ca5% Pd/$CeO_2$ (2Ca5PC), and a $CeO_2$ supported palladium catalyst 5% Pd/$CeO_2$ (5PC) which is a control sample devoid of elemental calcium. As shown in FIG. 1, the addition of elemental calcium to the $CeO_2$ supported palladium catalyst has increased the conversion of $CO_2$. By comparing Tables 2 and 3, it is found that the addition of elemental calcium to the catalyst (0.5% Ca5% Pd/$CeO_2$) has increased $CO_2$ conversion by at least 25-30%, 45-50%, and 20-30% relative to the control Pd catalyst without any metallic calcium at temperatures of 300° C., 325° C., and 350° C., respectively. With a molar ratio of $H_2$ to $CO_2$ at about 3:1, the conversion percentages of $CO_2$ are generally higher at higher temperatures (FIG. 1). FIG. 3 shows that at 325° C. and a molar ratio of $H_2$ to $CO_2$ at about 3:1, increasing the pressure has led to a decreased conversion percentage of $CO_2$ for the $CeO_2$ supported palladium catalyst. In addition, FIG. 5 demonstrates that at 350° C. and a molar ratio of $H_2$ to $CO_2$ at about 3:1, increasing the elemental calcium content from 0 to 0.5 wt % increases the conversion of $CO_2$, while further increasing the elemental calcium content above 0.5 wt % may decrease the conversion of $CO_2$. Furthermore, FIGS. 6 and 7 show that at 350° C., a molar ratio of $H_2$ to $CO_2$ at about 3:1, and a pressure of 1 or 30 bar, enhancing the GHSV value decreases the conversion of $CO_2$.

In one embodiment, 7-80 mol %, 10-70 mol %, 20-60 mol %, 30-50 mol %, or 35-45 mol % of the $CO_2$ present in the stream is converted to dimethyl ether and at least one side product selected from the group consisting of methanol, carbon monoxide, and methane. In other words, the percentage conversion of $CO_2$ is 7-80 mol %, 10-70 mol %, 20-60 mol %, 30-50 mol %, or 35-45 mol %.

As used herein, the selectivity of a gas phase product is a stoichiometric mol % of the product produced relative to a total mol of all products and side products generated. For example, the selectivity for dimethyl ether may be determined based on a total mol of dimethyl ether product as well as side products including methanol ($CH_3OH$), carbon monoxide (CO), and methane ($CH_4$). The percentage conversions for each product and/or side product are:

$$\text{DME } (CH_3OCH_3) \text{ selectivity } (\%) = \frac{\text{mole of } CH_3OCH_3 \times 100}{\text{mole of } CH_3OCH_3 + \text{mole of } CH_3OH + \text{mole of } CO + \text{mole of } CH_4}$$

-continued $$CO\ selectivity\ (\%) = \frac{mole\ of\ CO \times 100}{mole\ of\ CO + mole\ of\ CH_3OH + mole\ of\ DME + mole\ of\ CH_4}$$

$$CH_4\ selectivity\ (\%) = \frac{mole\ of\ CH_4 \times 100}{mole\ of\ CH_4 + mole\ of\ CH_3OH + mole\ of\ CO + mole\ of\ DME}$$

$$CH_3OH\ selectivity\ (\%) = \frac{mole\ of\ CH_3OH \times 100}{mole\ of\ CH_3OH + mole\ of\ DME + mole\ of\ CO + mole\ of\ CH_4}$$

Table 3 shows example selectivities of DME, CH$_3$OH, CO, and CH$_4$ using the CeO$_2$ supported palladium catalyst (0.5%/Ca5% Pd/CeO$_2$) at temperatures of 270-350° C., a pressure of 30 bar, and a GHSV of 2400 mL/g·hr. Over this temperature range, the selectivities for DME and carbon monoxide tends to increase as temperature increases, while the selectivities for methanol and methane tend to decrease. By comparing Tables 2 and 3, it is concluded that the addition of elemental calcium to the catalyst (0.5% Ca5% Pd/CeO$_2$) has increased the selectivity for DME by at least 45-55%, 20-30%, 12-18%, and 4-8% relative to the control Pd catalyst without any metallic calcium at temperatures of 270° C., 300° C., 325° C., and 350° C., respectively. FIG. 5 shows that at 350° C. and a molar ratio of H$_2$ to CO$_2$ at about 3:1, increasing the elemental calcium content in the CeO$_2$ supported palladium catalyst from 0 to 0.5 wt % increases the conversion of CO$_2$, while further increasing the elemental calcium content beyond 0.5 wt % may decrease the conversion of CO$_2$.

In one or more embodiments, a selectivity for dimethyl ether converted from the CO$_2$ ranges from 18-80%, 20-70%, 30-60%, or 40-50%. In one embodiment, a selectivity for dimethyl ether converted from the CO$_2$ of at least 70% may be achieved at reaction conditions of 325-400° C., with a molar ratio of H$_2$ to CO$_2$ at about 3:1, when using CeO$_2$ supported palladium catalyst disclosed herein in any of its embodiments.

Preferably the selectivities for other side products, such as carbon monoxide, methanol, and methane are 0-25%, preferably 0.1-20%, preferably 1-10%. In one or more embodiments, a selectivity for carbon monoxide converted from the CO$_2$ is less than 22%, preferably less than 17%, more preferably less than 11%. In one or more embodiments, a selectivity for methane converted from the CO$_2$ is less than 20%, preferably less than 9%, more preferably less than 3%. In one or more embodiments, a selectivity for methanol converted from the CO$_2$ is less than 30%, preferably less than 7%, preferably less than 0.1%.

The CeO$_2$ supported palladium catalyst disclosed herein may enable the conversion of CO$_2$ and H$_2$ to dimethyl ether to continue at a stable reaction rate for several hours. For a fixed flow rate of the stream, a fixed temperature, and a fixed H$_2$ to CO$_2$ molar ratio, the stability of the catalyst may be judged by monitoring a reactant conversion and/or a product selectivity over a period of time. In one embodiment, a conversion of CO$_2$ is maintained at a value of at least 25%, preferably at least 28%, more preferably at least 30% for a reaction period of at least 20 hours, preferably at least 40 hours, preferably at least 70 hours, even more preferably at least 90 hours. In a further embodiment, over this reaction period, the selectivity of DME may be maintained at a value of at least 68%, preferably at least 69%, more preferably at least 70%, while the conversion of CO$_2$ may be maintained at a value of at least 25%, preferably at least 28%, more preferably at least 30%. In one embodiment, this stable catalytic reaction rate may occur at reaction conditions such as a temperature of 250-400° C., 300-350° C., or about 325° C., a pressure of 1-30 bar, 2-20 bar, or 3-10 bar, a GHSV of 1,800-12,000 mL/g·hr, 2,500-10,000 mL/g·hr, or 6,000-9,000 mL/g·hr, and/or a molar ratio of H$_2$ to CO$_2$ at about 3:1.

In an alternative embodiment, the CeO$_2$ supported palladium catalyst disclosed herein in any of its embodiments may be used with a stream of CO$_2$ and H$_2$ but with reaction conditions (e.g. reaction temperature, pressure, GHSV, ratio between H$_2$ and CO$_2$) modified to produce more of a side product such as CO, CH$_3$OH, or CH$_4$.

The examples below are intended to further illustrate protocols for preparing, characterizing the CeO$_2$ supported palladium catalyst, and uses thereof, and are not intended to limit the scope of the claims.

Example 1

Preparation of Pd/CeO$_2$ Catalyst

The catalyst was synthesized via a sol-gel preparation method. In a typical preparation procedure for 2.0 g 5% Pd/CeO$_2$ sample, 0.2165 g Pd salt (palladium nitrate) and 4.794 g of cerium salt (cerium nitrate) were dissolved into separate beakers filled with 30 cm$^3$ deionized water. The solutions were heated at 50° C. for 15 minutes applying continuous stirring. An aqueous solution containing citric acid (7.5522 g in 30 cm$^3$ deionized water) present at 1:3 molar ratio of Pd and Ce metal ions to citric acid was also heated at 50° C. for 15 minutes. At first, the citric acid solution was added drop wise to the Ce salt solution, and the mixed suspension of Ce salt and citric acid was left to beat further at the same temperature for 10 minutes. Then the Pd salt solution was added drop wise into the mixed suspension of Ce Salt and citric acid. The resulting mixture was heated at a temperature of 90° C. using an electrically driven heating plate with necessary stirring, and was left for few hours until a gel-like mixture (brownish-yellow) started to appear. Then the mixture gel was placed in a water bath at 90° C. for 24 hours, later into an oven for 18 hours at 110° C. resulting in complete drying of the mixture gel. Afterwards, the dried mixture was first calcined at 300° C. for 2 hours in dry air then at 500 at 300° C. for 3 hours in an electrically driven furnace.

Example 2

Preparation of Ca—Pd/CeO$_2$ Catalyst

The catalyst was synthesized via a sol-gel preparation method. In a prototypical preparation procedure for 2.0 grams 0.5Ca5Pd/CeO$_2$ sample, 0.2165 g of Pd, 0.2362 g Ca and 4.6925 g of Ce salts were each dissolved into separate beakers filled with 30 mL deionized water, and heated at 50° C. for 15 minutes with continuous stirring. An aqueous solution of citric acid (8.0356 g, 30 mL deionized water) with citric acid present at 1:3 molar ratio of Pd and Ce metal ions to citric acid was also heated at 50° C. for 15 minutes. At first, the citric acid solution was added drop wise to the Ce salt solution and the mixed suspension of Ce salt and citric acid was left to heat further at the same temperature for 10 minutes. Then Pd salt solution was added drop wise into the mixed suspension of Ce salt and citric acid, which was followed by the addition of the Ca salt solution. The resulting mixture was heated at a temperature of 90° C. using an electrically driven heating plate with necessary stirring, and was left for few hours until a gel-like mixture (brownish-yellow) started to appear. Then the mixture gel was placed in a water bath at 90° C. for 24 hours, later into an oven for 18 hours at 110° C. resulting in complete drying of the mixture gel. Afterwards, the dried mixture was first calcined at 300° C. for 2 hours in dry air then at 500° C. for 3 hours in an electrically driven furnace.

Example 3

Catalytic Activity Testing of Ceria Supported Pd

Catalytic activity tests of the disclosed catalyst samples were carried out in a MA-Effi reactor (PID Eng.& Tech., Spain) equipped with Bronkhorst mass flow and temperature controllers. The catalyst samples were tested at a temperature range of 270-350° C. employing a gas mixture with composition of $CO_2:H_2=1:3$ (Vol. ratio). Prior to each reaction, samples were reduced at 550° C. with 20 cm$^3$ min$^{-1}$ H$_2$ flow (≥99.999%-Grade A) for one hour at atmospheric pressure.

In a general procedure, 0.5 grams of catalyst sample was placed into the stainless steel tubular reactor (i.d. 9.1 mm) and the temperature was raised in Ar flow of 15 cm$^3$ min$^{-1}$, (99.99%-Grade A) with a ramping rate of 5° C./min. Once the reaction temperature was established, the H$_2$ flow is turned on for 60 minutes. After reducing the catalyst sample, the temperature was brought back to reaction temperature under Ar flow.

The composition of product stream catalyzed by each sample was analyzed 3 hours after attaining reaction conditions (i.e. reaching a steady state) using an Agilent 7890 A GC equipped with a TCD detector with HayeSep Q packed column for $CO_2$, CO, and $CH_4$ analysis, and FID detector with HP-Pona capillary column (19091S-001E) for $CH_3OH$ and higher hydrocarbons analysis.

The data reported for conversion and selectivity was obtained by an average of three independent readings with an error of 3% taken after 3 hour of reaction. CO conversion and selectivity of products are defined as follows:

$$CO_2 \text{ Conversion (\%)} = \frac{(\text{Molar flow of } CO_{2\,in} - \text{Molar flow of } CO_{2\,out}) \times 100}{\text{Molar flow of } CO_{2\,in}} \quad (\text{Eq. 3})$$

$$CH_2OCH_3 \text{ Selectivity (\%)} = \frac{\text{Moles of } CH_3OCH_3 \times 100}{\text{Moles of } CH_3OH + \text{Moles of } CO + \text{Moles of } CH_4} \quad (\text{Eq. 4})$$

Example 4

Catalytic Activity Testing of CeO$_2$ Supported Ca—Pd Catalysts

The hydrogenation of CO$_2$ to DME was carried out in a similar manner with experimental setup as described in Example 4, with the addition of calcium to the catalyst by varying Ca content from 0.3 wt % to 2 wt %. The catalyst with calcium content of 0.5 wt % was further investigated by varying the gas hourly space velocity (GHSV) values.

Prepared catalysts were tested at various temperature, pressure and GHSV values. Activity and selectivity of DME and other side products at various operating conditions were investigated as shown in below tables and figures. The developed 5% Pd/Ceria catalyst showed excellent activity and selectivity even at very low temperature as compared to the conventional catalysts for DME synthesis. Importantly, as can be seen in data presented in Tables 2 and 3, addition of calcium greatly improved the overall catalyst activity and enhanced DME selectivity.

TABLE 2

Catalytic activity and selectivity results at different temperatures of 5% Pd/CeO$_2$ in DME synthesis via CO$_2$ hydrogenation.
(P = 30 bar, GHSV: 2400 mL/g · hr)

| 5%Pd/CeO$_2$ | | Selectivity | | | |
|---|---|---|---|---|---|
| Reaction Temperature, ° C. | % CO$_2$ Conv | % $S_{DME}$ | % $S_{CH3OH}$ | % $S_{CO}$ | % $S_{CH4}$ |
| 270 | 7.14 | 18.67 | 45.83 | 5.56 | 29.94 |
| 300 | 12.05 | 42.95 | 13.19 | 12.26 | 31.60 |
| 325 | 20.50 | 59.87 | 3.57 | 16.41 | 20.16 |
| 350 | 39.84 | 69.64 | 0.78 | 20.15 | 9.43 |
| 375 | 68.15 | 76.30 | 0.00 | 21.91 | 1.79 |

TABLE 3

Catalytic activity and selectivity results at different temperatures with 0.5% Ca 5% Pd/CeO$_2$ catalyst for DME synthesis from CO$_2$ hydrogenation.
(P = 30 bar, GHSV: 2400 mL/g · hr)

| 0.5% Ca 5% Pd/CeO$_2$ | | Selectivity | | | |
|---|---|---|---|---|---|
| Reaction Temperature, ° C. | % CO$_2$ Conv | % $S_{DME}$ | % $S_{CH3OH}$ | % $S_{CO}$ | % $S_{CH4}$ |
| 270 | 73 | 38.2 | 30.4 | 11.2 | 20.2 |
| 300 | 17.8 | 57.1 | 7.0 | 16,9 | 18.9 |
| 325 | 38.0 | 70.0 | 0 | 21.9 | 9.2 |
| 350 | 53.3 | 74.6 | 0 | 21.96 | 3.4 |

Example 5

Effect of Pressure on Catalytic Activity 0.5% Ca5% Pd/CeO$_2$ exhibited superior catalyst performance at atmospheric pressure, which implied that the currently disclosed catalyst is highly active for synthesizing DME from CO$_2$ hydrogenation and requires no additional pressure at all. Just to see the effect of pressure, the 0.5% Ca5% Pd/CeO$_2$ catalyst was tested at various pressures by keeping the GHSV and temperature of the reaction constant. The observed results of catalytic activity are presented in FIG. 3.

Example 6

Figure 4:
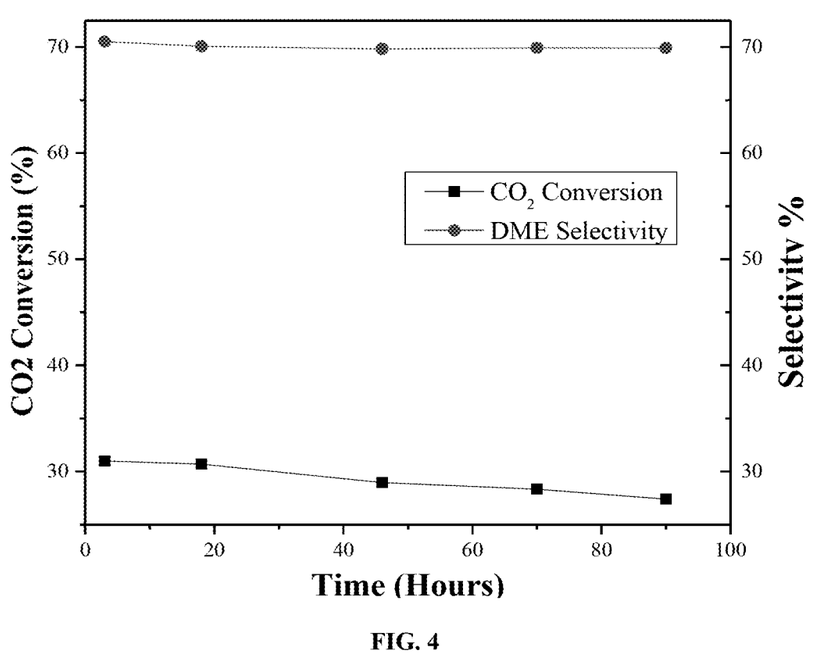
FIG. 4 shows the stability of $CO_2$, conversions and product selectivities of DME synthesis catalyzed by 0.5% Ca5% Pd/$CeO_2$ at a temperature of 325° C., an operating pressure of 30 bar, and a GHSV of 2400 mL/g·hr.

Catalyst Stability Analysis 0.5% Ca5% Pd/CeO$_2$ catalyst was also investigated in long run stability analysis for reactions synthesizing DME from CO$_2$ hydrogenation. The temperature and pressure of the reaction were set at 325° C. and 30 bar, respectively. Data was collected for 90 hours of continuous reaction and plotted as shown in FIG. 4. There was a slight decrease in CO$_2$ conversion with reaction time progressing, but the selectivity of the catalyst remained almost constant over the period investigated, which showed that the developed catalysts is quite stable and does not sinter quickly.

Example 7

Promotion of Calcium Content Addition of calcium has significantly enhanced the overall conversion of CO$_2$ and selectivity of DME of the catalyst. Based on FIG. 5, we can determine a proper amount of calcium that needs to be added to the disclosed catalyst in order to achieve maximum reaction activity and selectivity.

Example 8

Effect of GHSV at 30 Bar

The disclosed catalyst was also investigated at 350° C. and 30 bar pressure with changing gas hourly space velocity (GHSV) values and the results are presented in FIG. 6. It can be noted that varying the GHSV value has a profound effect on $CO_2$ conversion and DME selectivity, as both of which decreased with increasing GHSV. This pattern shows that reduction in contacting time significantly affects the conversion and selectivity.

Example 9

Effect of GHSV at Atmospheric Pressure

As shown in FIG. 7, the effect of GHSV on the disclosed catalyst (0.5Ca5PC) was also investigated at 325° C. and atmospheric pressure.

Example 10

The catalyst for the one-step selective synthesis of DME from $CO_2$ hydrogenation reaction is composed of ceria supported palladium nanoparticles where the content of palladium is 5 wt %. The currently disclosed catalyst further includes calcium particles decorated with palladium over ceria support. The content of calcium is varied from 0.3 wt % to 2 wt %.

The active component for the reaction of $CO_2$ hydrogenation to DME involves Pd and Ca aided in enhancing the overall activity and selectivity of the disclosed catalyst. Pd and Ca particles were deposited over ceria by employing the sol-gel preparation method using citric acid as a chelating agent. Catalyst synthesis includes a calcination stage, which involves first 2 hours at 300° C., then 3 hours at 500° C. in dry air.

The catalyst was tested for catalyzing $CO_2$ to DME reaction at a temperature range of 270 to 400° C. and a pressure of 30 bar. The selectivity of DME using the catalyst has increased to above 75% with a $CO_2$ conversion of above 50% using a feed ratio $CO_2$:$H_2$=1:3.

Example 11

Advantages

The disclosed catalyst is highly active and selective for DME synthesis compared to the conventional catalysts used or previously reported. The advantages of the disclosed catalyst includes: (i) high $CO_2$ conversions even at low pressure, (ii) high production yields of DME, (iii) low CO selectivities, (iv) low $CH_4$ selectivities, and (v) low operating pressures.

The invention claimed is:

1. A $CeO_2$ supported palladium catalyst, comprising:
   0.05-2 wt % of a promoter comprising Ca;
   1-8 wt % of a catalytic material comprising Pd; and
   90-98 wt % of $CeO_2$, each relative to a total weight of the $CeO_2$ supported palladium catalyst,
   wherein:
   the $CeO_2$ supported palladium catalyst has an atomic ratio of palladium to calcium ranging from 2:1 to 6:1; and
   the promoter and the catalytic material are deposited on the $CeO_2$.

2. The $CeO_2$ supported palladium catalyst of claim 1, wherein the promoter and the catalytic material are in the form of particles.

3. The $CeO_2$ supported palladium catalyst of claim 1, which has a surface area of 50-100 $m^2/g$.

4. The $CeO_2$ supported palladium catalyst of claim 1, which has an atomic ratio of cerium to palladium ranging from 7:1 to 50:1.

5. A method of preparing the $CeO_2$ supported palladium catalyst of claim 1, the method comprising:
   heating an aqueous solution of a Ce(III) salt and citric acid to form a first mixture;
   mixing the first mixture with an aqueous solution of a Pd(II) salt and an aqueous solution of a Ca(II) salt to form a second mixture;
   heating the second mixture to form a gel;
   drying the gel to form a dried powder;
   calcining the dried powder in air to form a pre-catalyst; and
   subjecting the pre-catalyst to $H_2$ gas thereby forming the $CeO_2$ supported palladium catalyst.

6. The method of claim 5, wherein a molar ratio of the citric acid to a total content of the Ce(III) salt and the Pd(II) salt ranges from 2:1 to 10:1.

7. The method of claim 5, wherein a molar ratio of the Pd(II) salt to the Ca(II) salt ranges from 1:50 to 75:1, and a molar ratio of the Ce(III) salt to the Pd(II) salt ranges from 5:1 to 500:1.

8. The method of claim 5, wherein the Ce(III) salt is cerium(III) nitrate.

9. The method of claim 5, wherein the Pd(II) salt is palladium(II) nitrate.

10. The method of claim 5, wherein the Ca(II) salt is calcium(II) nitrate.

11. A process of producing dimethyl ether from $CO_2$ and $H_2$, the process comprising:
    contacting a stream comprising $CO_2$ and $H_2$ with the $CeO_2$ supported palladium catalyst of claim 1 in a reactor, thereby producing dimethyl ether and at least one side product selected from the group consisting of methanol, carbon monoxide, and methane,
    wherein a molar ratio of the $H_2$ to the $CO_2$ ranges from 1:1 to 6:1.

12. The process of claim 11, wherein the stream has a gas hourly space velocity of 1,800-12,000 mL/g·hr.

13. The process of claim 11, wherein the stream is contacted with the $CeO_2$ supported palladium catalyst at a temperature of 250-400° C.

14. The process of claim 11, wherein the stream is contacted with the $CeO_2$ supported palladium catalyst at a pressure of 1-30 bar.

15. The process of claim 11, wherein the stream further comprises an inert carrier gas.

16. The process of claim 11, wherein 7-80 mol % of the $CO_2$ present in the stream is converted to dimethyl ether and the at least one side product.

17. The process of claim 11, wherein a selectivity for dimethyl ether converted from the $CO_2$ ranges from 18-80%.

18. The process of claim 11, wherein a selectivity for carbon monoxide converted from the $CO_2$ is less than 22%, a selectivity for methane converted from the $CO_2$ is less than 20%, and a selectivity for methanol converted from the $CO_2$ is less than 30%.

19. The process of claim 11, wherein a conversion of $CO_2$ and a selectivity for dimethyl ether are maintained over a reaction period of 90 or more hours.

20. A process of producing dimethyl ether from $CO_2$ and $H_2$, the process comprising:
   contacting a stream comprising $CO_2$ and $H_2$ with the $CeO_2$ supported palladium catalyst of claim 1 in a reactor, thereby producing dimethyl ether and at least one side product selected from the group consisting of methanol, carbon monoxide, and methane,
   wherein a molar ratio of the $H_2$ to the $CO_2$ ranges from 1:1 to 6:1.

21. The process of claim 20, wherein the stream is contacted with the $CeO_2$ supported palladium catalyst at a temperature of 250-400° C., at a pressure of 1-30 bar, and at a gas hourly space velocity of 1,800-12,000 mL/g·hr.

22. The process of claim 20, wherein a selectivity for dimethyl ether converted from the $CO_2$ ranges from 18-80%, a selectivity for carbon monoxide converted from the $CO_2$ is less than 22%, a selectivity for methane converted from the $CO_2$ is less than 20%, and a selectivity for methanol converted from the $CO_2$ is less than 30%.

* * * * *